United States Patent [19]
Bastioli et al.

[11] Patent Number: 5,902,262
[45] Date of Patent: May 11, 1999

[54] COTTON BUDS STICKS OF PLASTIC MATERIAL

[75] Inventors: Catia Bastioli; Giuseppe Raffa; Angelos Rallis, all of Novara, Italy

[73] Assignee: Novamont S.p.A., Milan, Italy

[21] Appl. No.: 08/554,560

[22] Filed: Nov. 6, 1995

[30] Foreign Application Priority Data

Dec. 23, 1994 [IT] Italy .................................. MI94A2616

[51] Int. Cl.$^6$ .................................................. A61M 35/00
[52] U.S. Cl. ................................................................ 604/1
[58] Field of Search ................................... 604/1, 11, 12, 604/15, 370, 904, 364, 2, 3

[56] References Cited

U.S. PATENT DOCUMENTS 4,820,259   4/1989   Stevens .

FOREIGN PATENT DOCUMENTS

| | | |
|---|---|---|
| 445683 | 6/1927 | Germany . |
| 827697 | 1/1952 | Germany . |
| 1183641 | 12/1964 | Germany . |
| 301572 | 9/1927 | United Kingdom . |
| WO 92/19680 | 11/1992 | WIPO . |

OTHER PUBLICATIONS

European Search Report dated Apr. 8, 1997 for EP 95 11 6392 with Annex.

*Primary Examiner*—Robert A. Clarke
*Attorney, Agent, or Firm*—Bryan Cave LLP

[57] ABSTRACT

Stick with cotton buds for hygienic use, which are disintegrable in water and rapidly biodegradable, manufactured from a thermoplastic material obtained from natural polymeric substances which are biodegradable and water soluble when in their thermoplastic state or from biodegradable, water soluble synthetic polymers.

17 Claims, No Drawings

COTTON BUDS STICKS OF PLASTIC MATERIAL

FIELD OF THE INVENTION

The present invention relates to sticks with cotton buds suitable for hygienic and cosmetic use, in particular for ears hygiene, disintegrable in water and undergoing rapid biodegradation, obtained from natural substances of polymeric nature rendered thermoplastic or from synthetic polymers.

BACKGROUND OF THE INVENTION

The sticks of plastic material provided with one or two end cotton buds, presently used, constitute a serious problem for water purification facilities because they are often disposed of through the drainage system, causing the obstruction of the filters of such facilities and a visual pollution of water and soil caused by the purified water and active sewage sludges which contain them.

At present, said plastic sticks are obtained by means of an extrusion technology according to which small tubes of approximately 2.5–3 mm of diameter are extruded at extrusion rates of 50–100 m/minute.

The resulting productivity is of approximately 700–1300 sticks per minute. The extruded tube is then calibrated by causing it to run first through a duct, after being sprayed with water, and then through a water bath, before being cut.

This technology is difficultly applied to the preparation of water dispersible sticks based on natural or synthetic water-soluble polymeric substances because water calibration and cooling would become unfeasible and the productivity would furthermore result very limited with air cooling.

SUMMARY OF THE INVENTION

It has now been found that water disintegrable and rapidly biodegradable cotton bud sticks can be prepared by injection moulding starting from natural polymeric substances which, when converted into the thermoplastic state, are water soluble or capable of getting dispersed in water and undergoing rapid biodegradation or from synthetic polymers water soluble or capable of getting dispersed in water and undergoing rapid biodegradation.

DETAILED DESCRIPTION

Examples of natural substances usable for preparing the sticks comprise:

starch deriving from seeds, roots or beans or grits, from various genotypes, with high or low content of amylose, in its native state or chemically or physically modified, hydrolysed, oxidized, or crosslinked;

cellulose derivatives, such as carboxylmethylcellulose;

gelatin;

alginates;

chitosan;

pullulan;

pectin;

carayenanes;

proteins (zein, gluten, soy proteins), natural resins based on shellac, rosin acid;

natural rubbers;

polyaspartates;

The various starch types are the preferred starting substances. Starch can be used in mixture with the natural substances indicated above, in particular with gelatin from animal origin, zein, pullulan, pectin.

Starch, or the other natural substances, can be mixed with a synthetic polymer which can be compatible or not with starch, such as polyvinyl alcohol, polyvinyl acetate with different hydrolysis degree, polyoxyalkylenes, or insoluble synthetic polymers, such as ethylene-vinyl alcohol, ethylenevinyl acetate, ethylene-acrylic esters, or acrylic acid copolymers, thermoplastic polyesters, preferably aliphatic polyesters such as polycaprolactone polyester-polyurethanes, polyester-polyurethane-polyurea copolymers, lactic acid polymers and copolymers, cellulose acetate, starch esters with substitution degree from 0.1 to 2, possibly in the presence of their specific plasticizers. Polymers of this types are disclosed in Italian patent application with filing No. MI94A000228, the disclosure of which is incorporated hereto by reference.

These polymers are added in amounts lower than about 30% by weight, preferably up to about 20% by weight.

The water soluble or water dispersible biodegradable synthetic polymers comprise polyvinyl alcohol with various hydrolysis degrees, preferably with degree comprised between 80 and 90% as for example Polyviol W 40/140 (hydrolysis degree 87, MW=100.000) manufactured by Waker, or the Gohsend grades GH-23, GH20 or KH-17 of Nippon Goshei, or a preplastified polyvinylalcohol such as the Vinex of Air Products; polyoxymethylene or polyoxyethylene, polyethyloxazoline polyvinylpirrolidone, polyaspartates.

The transformation of the natural substances of the above indicated type to yield thermoplastic materials is carried out in heated extruders (extrusion-cooking), or in any devices which may secure temperature and shear stress conditions which are the proper ones to cause the material to become thermoplastic, by operating in the presence of water and/or a plasticizer, at a temperature comprised within the range from 80° C. to 210° C.

Preferably, the total amount of water and plasticizer is lower than 25% by weight with respect to the natural fraction.

The usable plasticizer comprise, besides water, polyols with 1–20 recurrent hydroxylated units each containing from 2 to 6 carbon atoms, which may also be partially substituted.

This type of compounds are disclosed in patent application WO 92/19680, the disclosure of which is incorporated hereto by reference. Preferred plasticizer are glycerol, glycerol acetate, polyethylene and polypropylene glycol, sorbitol, sorbitol acetate, ethoxylated sorbitol, citric acid.

The addition of lubricants is advantageous in order to obtain a high productivity of the injection moulding process.

The usable lubricants are based on fatty chains such as oleic acid, stearic acid, palmitic acid, erucic acid, also converted into esters, amides, salts and ethers, in the case of reaction with alkaline oxides.

Suitable lubricants comprise steramide, stearyl alcohol, calcium stereate, mono- di- and triglycerides or oleates of polyols also containing alkylenoxide units.

Fillers of vegetable origin can be added such as (cellulose fibres, dried beet flesh, yeast shells, wood, rice husk) or of mineral origin such as talk, silica, silicates, carbonates.

In order to reduce the weight, foaming agents can be added which rendering microfoamed the end product.

The stick shapes are tailored to the moulding process in order to obtain high productivity values.

Solid forms, tubular forms with tapered bore to allow the sticks to be de-moulded, polygonal forms, lobed-cross-section forms, can be used and in general any form compatible with the injection moulding process. The mouldability of the material is preferably selected to allow production cycles shorter than 15 seconds and preferably than 10 seconds.

The injection moulding can be carried out with riser, sprue, hot-channel, hot-chamber systems, or still other moulding systems. The application of the cotton buds on both stick ends is carried out according to well-known methods, by treating, e.g., the ends of sticks either with adhesives, or mechanically, and/or with water in order to cause the cotton-wool to be retained.

The absorbent buds wound around one or both stick ends, are preferably formed by cotton-wool. Other non-woven natural fibres can be used, such as rayon fibres, possibly in mixture with minor proportion of synthetic fibres.

Cotton can be bleached or unbleached.

The sticks for aural hygiene generally have a cylindrical form, 7–10 cm long, with a diameter of 2–3 mm.

The following examples are given to illustrate the invention but not to limit it. Unless otherwise indicated, the parts and percentages are by weight.

EXAMPLE 1

80 parts of mais starch Globe 3401 ex Cerestar, 10 parts of polyvinyl alcohol, 9.6 parts of water, 0.15 parts of glycerol monooleate, 0.25 parts of calcium stearate were fed to a twin-screw extruder APV 2030 with L:D (ratio of screw length to screw diameter)=30. The temperature profile used was 60° C.–100° C.–150° C.–3×105° C.–2×165° C.–155° C.

At the twenty-fifth diameter, the product was vented in order to reduce its water content to 12%.

The obtained pellets were fed to a 60 ton Sandretto injection press.

The used mould was a sprue mould with 20 cavities and two extractors for each cavity at the height of ¼ and ⅓ each cavity. The hollows were solid cylinders of 7.35 cm of length and 2.5 mm of diameter, with rounded ends. The mould was water cooled.

The temperature profile used was flat and set at 165° C.

The moulding cycle was of 9 seconds.

The resulting pieces were provided with cotton buds by using the conventional cotton-wool application system with mechanical erosion of stick ends in order to improve the cotton adhesion.

One of so obtained pieces was dipped in 100 cc of water and was kept with slow stirring; two hours later, the piece was completely disintegrated. When the pieces were submitted to Sturm OECD 301 test with sodium acetate as the reference substance, a biodegradability higher than 70% in 5 days was reached, as required for soluble products which must be disposed off through water reclaiming facilities.

EXAMPLE 2

The preparation was carried out as in Example 1, with the difference that 3% of PVOH was replaced EVOH (ethylene/vinyl alcohol copolymer) containing 44% of ethylene by mole and having a hydrolysis degree higher than 99.8%.

The resulting product disintegrated in water under slow mechanical stirring, however less easily than the product from Example 1.

EXAMPLE 3

The process is carried out as in Example 1, with the difference that 5% of PVOH is replaced by EVOH. The resulting product was still disintegrating in water in a time of approximately 3 hours.

EXAMPLE 4

The preparation is carried out as in Example 1, with the difference that 5% of starch is replaced by 5% of Estane 54351 (Goodrich), a copolymer constituted by low molecular weight polycaprolactone segments bonded by urethane linkages.

The product resulted to be still disintegrable in water.

EXAMPLE 5

The run was carried as in Example 1, with the difference that a formulation is used which contains 85 parts of starch, 5 parts of Estane 54351, 9.6 parts of water, 0.1 parts of monoglyceride and 0.4 parts of stearamide. The product was disintegrable in water and biodegradable according to Sturm test in 5 days.

EXAMPLE 6

The run is carried out as in Example 1, with the difference that 40 parts of starch were replaced by zein.

The resulting product showed a good disintegrability in water.

EXAMPLE 7

The preparation is carried out as in Example 1, with the difference that 40 parts of starch were replaced with animal gelatin. The product proved to be disintegrable in water within the times observed for the products of the other examples.

EXAMPLE 8

The run is carried out as in Example 1, but with starch being completely replaced by pullulan. The resulting product is even more easily dispersible in water than the product of Example 1.

EXAMPLE 9

80 parts of wheat starch SF 20006 ex Cerestar, 3 parts of starch acetate with a substitution degree of 1.5, 5 parts of cellulose acetate, 1.5 parts of glycerol monoacetate, 9.5 parts of water, 0.1 part of monoglyceride and 0.3 part of stearyl alcohol are treated as in Example 1. The so obtained product results to be dispersible.

EXAMPLE 10

The run is carried out as in Example 1, with the difference that 5 parts of water are replaced by glycerol. By venting, the water content was reduced to 7%. The product resulted to be very flexible and with extremely good water dispersibility.

EXAMPLE 11

The run is carried out as in Example 10, with 5% of PVOH being replaced by Union Carbide 787 polycaprolactone.

The product resulted to be mouldable and water dispersible.

EXAMPLE 12

84% Eurilon VII starch with a high content of amylose, 5% of starch acetate with substitution degree 1.5, 4% of glycerol and 1% of diacetine, 5.6% of water, 0.1% of glycerol monooleate and 0.3% of calcium stearate were treated as in Example 1.

The product resulted to be mouldable with a 12-second cycle and proved to be disintegrable in water within less than 2 hours.

EXAMPLE 13

The run is carried out as in Example 1, with the difference that 10 parts of cellulose fibres and 5 parts of glycerol are added. After extrusion, the product contained about 8% of water. The mouldability was good, even if it was worst than non-filled products. Water disintegrability was good.

EXAMPLE 14

The product from Example 1 was moulded on a pilot single cavity mould characterized by a 7.3 cm long cavity of tubular shape with an outer diameter of 2.7 mm and an inner diameter which was of 1 mm at an end and 0.8 mm at the other end, in order to supply the necessary taper for demoulding. The piece was moulded without problems on the single-cavity mould.

We claim:

1. A biodegradable stick covered with cotton buds, particularly suitable for hygienic use, the biodegradable stick having a disintegration rate in water at room temperature of about 2–3 hours, the biodegradable stick being obtained from a material selected from the group consisting of natural polymeric substances which are biodegradable and water soluble or water dispersible when converted into the thermoplastic state, synthetic biodegradable water dispersible polymers, or mixtures thereof.

2. The biodegradable stick according to claim 1, wherein the biodegradable stick are obtained from starch.

3. The biodegradable stick according to claim 1, wherein the biodegradable sticks are obtained from natural substances selected from the group consisting of gelatin, alginate, chitosan, pullulan, proteins, and natural resins.

4. The biodegradable stick according to claim 1, wherein the natural substance is a mixture of starch and a natural substance selected from the group consisting of gelatin, alginate, chitosan, pullulan, proteins, and natural resins.

5. The biodegradable stick according to claim 1, wherein a synthetic biodegradable polymer compatible with starch is mixed, in an amount up to 30% by weight with respect to the natural polymeric substance, with the natural polymeric substance.

6. The biodegradable stick according to claim 1, wherein a synthetic biodegradable polymer incompatible with starch is mixed, in an amount up to 30% by weight with respect to the natural polymeric substance, with the natural polymeric substance.

7. The biodegradable stick according to claim 1, wherein a synthetic biodegradable polymer is mixed, in an amount up to 30% by weight with respect to the natural polymeric substance, with the natural polymeric substance, the synthetic biodegradable polymer being selected from the group consisting of polyvinyl alcohol, polyvinyl acetates with varying degrees of hydrolysis, polyoxyalkylenes, polyaspartates, polyvinylpyrrolidone, ethylene-vinyl alcohol, ethylene-vinyl acetates, starch esters, ethylene acrylic esters or acrylic acid copolymers, aliphatic polyesters, polyureas, aliphatic polyurethanes, polyester-polyurethane, polyester-polyurethane-polyurea, and polyester/polyether copolymers.

8. The biodegradable stick according to claim 7, wherein the aliphatic polyester is selected from the group consisting of polycaprolactone, polyesterurethanes, and polyester/polyether copolymers.

9. The biodegradable stick according to claim 1, wherein the synthetic biodegradable water dispersible polymer is selected from the group consisting of polyvinylalcohol, polyvinylpyrrolidone, and polyaspartate.

10. The biodegradable stick according to claim 1, wherein the natural polymeric substance, or the synthetic biodegradable water dispersible polymers is used in mixture with fillers of vegetable origin or mineral origin.

11. A biodegradable stick covered with cotton buds, particularly suitable for hygienic use, the biodegradable stick having a disintegration rate in water at room temperature of approximately 2–3 hours, the biodegradable sticks being obtained from a material selected from the group consisting of natural polymeric substances which are biodegradable and water soluble or water dispersible when converted into the thermoplastic state, or synthetic biodegradable water dispersible polymers, wherein the natural polymeric substance is rendered thermoplastic by means of an extrusion-cooking process in which the natural polymeric substance is extruded under shear stress and temperature conditions sufficient to render the natural substance thermoplastic, operating in the presence of water and/or a plasticizer in amounts up to a total of 25% by weight.

12. The biodegradable stick according to claim 11, wherein the plasticizer is selected from the group consisting of polyols with 1–20 hydroxylated recurrent units each containing from 2–6 carbon atoms, derivatives of such polyols selected from the group consisting of ether derivatives, thioether derivatives, organic and inorganic ester derivatives, acetate and amino derivatives, the reaction products of such polyols with chain extenders and polyol oxidation products containing at least one aldehydic group or carboxylic group.

13. The biodegradable stick according to claim 12, wherein the plasticizer is selected from the group consisting of glycerol, diacetine, ethylene or propylene glycol, sorbitol, sorbitol ethoxylate, and sorbitol acetate.

14. The biodegradable stick according to claim 11, wherein the biodegradable stick further comprise a lubricant.

15. A process for preparing biodegradable sticks for hygienic use from a biodegradable natural thermoplastic material or from a biodegradable synthetic thermoplastic material having a disintegration rate in water at room temperature of about 2–3 hours, comprising the step of injection extruding the natural or synthetic thermoplastic material using production cycles shorter than 15 seconds.

16. A process for preparing biodegradable sticks for hygienic use according to claim 15, wherein the biodegradable stick is molded to form a solid cylindrical shape, or a tubular shape with an inner taper, or a tubular shape with a polygonal or lobed cross-section.

17. A biodegradable stick covered with cotton buds, particularly suitable for hygienic use, the biodegradable stick having a disintegration rate in water at room temperature of about 2–3 hours, wherein a synthetic biodegradable polymer is mixed, in an amount up to 30% by weight with respect to starch, the synthetic biodegradable polymer being selected from the group consisting of polyvinyl alcohol, ethylene-vinyl alcohol copolymer, and mixtures thereof.

* * * * *